(12) United States Patent
Hodrinsky et al.

(10) Patent No.: US 11,253,842 B1
(45) Date of Patent: Feb. 22, 2022

(54) TITANIUM DIOXIDE CONTAINING PEROXO TITANIUM COMPLEX AND METHODS OF MANUFACTURING AND APPLICATION OF THE SAME

(71) Applicant: TiCoat, Inc., Mansfield Center, CT (US)

(72) Inventors: Todd W. Hodrinsky, Mansfield Center, CT (US); Marcel Janse, Hasselt (BE)

(73) Assignee: TiCoat, Inc., Mansfield Center, CT (US)

(*) Notice: Subject to any disclaimer, the term of this patent is extended or adjusted under 35 U.S.C. 154(b) by 0 days.

(21) Appl. No.: 17/221,709

(22) Filed: Apr. 2, 2021

(51) Int. Cl.
| | |
|---|---|
| *B01J 21/06* | (2006.01) |
| *B01J 23/72* | (2006.01) |
| *B01J 35/00* | (2006.01) |
| *B01J 35/02* | (2006.01) |
| *B01J 37/02* | (2006.01) |
| *B01J 37/04* | (2006.01) |
| *A61L 2/232* | (2006.01) |
| *A61L 101/26* | (2006.01) |

(52) U.S. Cl.
CPC ............ *B01J 23/72* (2013.01); *A61L 2/232* (2013.01); *B01J 21/063* (2013.01); *B01J 35/004* (2013.01); *B01J 35/0006* (2013.01); *B01J 35/0013* (2013.01); *B01J 35/026* (2013.01); *B01J 37/024* (2013.01); *B01J 37/0217* (2013.01); *B01J 37/0221* (2013.01); *B01J 37/0228* (2013.01); *B01J 37/04* (2013.01); *A61L 2101/26* (2020.08)

(58) Field of Classification Search
CPC ...... B01J 21/063; B01J 23/72; B01J 35/0006; B01J 35/0013; B01J 35/004; B01J 35/026; B01J 37/0217; B01J 37/0221; B01J 37/0228; B01J 37/024; B01J 37/04; A61L 2/232
See application file for complete search history.

(56) References Cited

U.S. PATENT DOCUMENTS

| | | | | |
|---|---|---|---|---|
| 5,021,392 | A * | 6/1991 | Daly | ...................... B01J 21/063 |
| | | | | 502/439 |
| 6,027,797 | A * | 2/2000 | Watanabe | ........... C03C 17/3411 |
| | | | | 428/312.8 |

(Continued)

FOREIGN PATENT DOCUMENTS

EP        1 052 027 B1      2/2007

OTHER PUBLICATIONS

Ichinose, H. et al. "Photocatalytic activities of coating films prepared from peroxotitanic acid solution-derived anatase sols", 1998, Journal of the Ceramic Society of Japan, 106:3, pp. 344-347.

(Continued)

*Primary Examiner* — Cam N. Nguyen
(74) *Attorney, Agent, or Firm* — Wiggin and Dana LLP; Anthony D. Sabatelli; Brian A. Pattengale (57) ABSTRACT

A surface coating composition may include titanium dioxide optionally combined with copper oxide to permanently bind to any surface to create a long lasting, self-cleaning, deodorizing, and antimicrobial surface, and preparation method thereof. A method of continuous flow process to create anatase $TiO_2$ crystals with particle sizes ranging from about 0.1 nm to about 200 nm, or further ranging from about 0.1 nm to about 20 nm in size.

23 Claims, 4 Drawing Sheets

(56) References Cited

U.S. PATENT DOCUMENTS

| | | | |
|---|---|---|---|
| 6,107,241 A | 8/2000 | Ogata et al. | |
| 6,210,779 B1* | 4/2001 | Watanabe | B01J 37/0215 |
| | | | 428/208 |
| 6,235,401 B1 | 5/2001 | Ogata et al. | |
| 6,344,277 B1 | 2/2002 | Ogata et al. | |
| 6,344,278 B1 | 2/2002 | Ogata et al. | |
| 6,379,811 B2 | 4/2002 | Ogata et al. | |
| 6,429,169 B1* | 8/2002 | Ichinose | B01J 35/002 |
| | | | 502/350 |
| 6,602,918 B1 | 8/2003 | Ichinose | |
| 6,884,752 B2 | 4/2005 | Andrews | |
| 7,205,049 B2 | 4/2007 | Andrews | |
| 7,261,942 B2 | 8/2007 | Andrews | |
| 7,335,245 B2 | 2/2008 | He et al. | |
| 7,431,903 B2* | 10/2008 | Koyanagi | B01J 21/063 |
| | | | 423/610 |
| 7,659,226 B2* | 2/2010 | Tucker, II | B01J 37/10 |
| | | | 502/300 |
| 7,727,500 B2 | 6/2010 | Andrews | |
| 7,879,757 B2 | 2/2011 | Kuroda et al. | |
| 7,887,780 B2 | 2/2011 | Seok et al. | |
| 8,025,976 B2 | 9/2011 | Ogata et al. | |
| 8,038,970 B2 | 10/2011 | Andrews | |
| 8,207,085 B2 | 6/2012 | Kuroda et al. | |
| 8,377,414 B2* | 2/2013 | Torardi | H01M 4/131 |
| | | | 423/610 |
| 8,518,174 B2 | 8/2013 | Ogata et al. | |
| 8,741,431 B2 | 6/2014 | Mizue et al. | |
| 8,753,684 B2 | 6/2014 | Pfluecker et al. | |
| 8,791,044 B2* | 7/2014 | Varma | B01J 35/004 |
| | | | 502/350 |
| 8,986,580 B2 | 3/2015 | Furudate et al. | |
| 9,352,299 B2* | 5/2016 | Kerrod | B01J 37/08 |
| 9,463,436 B2 | 10/2016 | Furudate et al. | |
| 9,522,389 B2 | 12/2016 | Sambandan et al. | |
| 9,555,406 B2 | 1/2017 | Sambandan et al. | |
| 9,918,475 B2 | 3/2018 | Moros et al. | |
| 10,463,046 B2 | 11/2019 | Moros et al. | |
| 10,737,241 B2 | 8/2020 | Furudate et al. | |
| 2004/0265218 A1* | 12/2004 | Kieda | B01J 35/004 |
| | | | 423/610 |
| 2004/0265887 A1* | 12/2004 | Herman | C12Q 1/683 |
| | | | 435/6.14 |
| 2006/0110317 A1* | 5/2006 | Torardi | B01J 21/063 |
| | | | 423/610 |
| 2006/0263291 A1* | 11/2006 | Torardi | C09C 1/3607 |
| | | | 423/608 |
| 2011/0092359 A1* | 4/2011 | Kuroda | B01J 35/004 |
| | | | 502/164 |
| 2016/0228850 A1* | 8/2016 | Kerrod | B01J 37/036 |
| 2020/0071185 A1* | 3/2020 | Li | C01G 23/053 |

OTHER PUBLICATIONS

Ichinose, H. et al. "Properties of peroxotitanium acid solution and peroxo-modified sol derived from peroxotitanium hydrate", 2001, Journal of Sol-Gel Science and Technology, 22, pp. 33-40.

Ichinose, H. et al. "Properties of anatase films for photocatalyst from peroxotitanic acid solution and peroxo-modified anatase sol", 1996, Journal of the Ceramic Society of Japan, 104:10, pp. 914-917.

Ichinose, H. et al. "Synthesis of peroxo-modified anatase sol from peroxo titanic acid solution", 1996, Journal of the Ceramic Society of Japan, 104:8, pp. 715-718.

Kobayashi, M. et al. "Synthesis of titanium dioxide nanocrystals with controlled crystal- and micro-structures from titanium complexes", 2013, 3, article 23, pp. 1-10.

Miyauchi, M. et al. "Antiviral effect of visible light-sensitive CuxO/TiO2 photocatalyst", 2020, Catalysts, 10, article 1093, pp. 1-19.

Moongraksathum, B. et al. "Photocatalytic antibacterial effectiveness of Cu-doped TiO2 thin film prepared via the peroxo sol-gel method", 2018, Catalysts, 8, article 352, pp. 1-10.

* cited by examiner

TITANIUM DIOXIDE CONTAINING PEROXO TITANIUM COMPLEX AND METHODS OF MANUFACTURING AND APPLICATION OF THE SAME

TECHNICAL FIELD

The products and methods disclosed herein are related to a method for preparation of a titanium dioxide ($TiO_2$) photocatalyst and to a method of manufacturing and applying a surface coating composition comprising either titanium dioxide particles, or copper combined with titanium dioxide particles, to permanently bind to any surface to create a long lasting, self-cleaning, deodorizing, and antimicrobial surface.

BACKGROUND

Titanium dioxide films and powders have attracted attention for decades for use as photocatalysts for decomposition of organics and microorganisms using light, oxygen, and water to create hydroxyl radicals and superoxide anions.

The challenge has been to affix these titanium dioxide particles to substrates so they would be permanently attached to the surfaces. The most common types of titanium dioxide are rutile and anatase. Anatase is the most desirable for the purpose of decomposition effectiveness. Anatase films are highly desirable for this task and have typically been prepared by various methods of vapor deposition or sol-gel by dipping materials in the coating under controlled temperatures and environments. Other methods use $TiO_2$ in powder form where the surface requires baking or electrolysis to adhere the Titanium dioxide particles to substrates.

Traditional methods of applying sol-gel and liquid coatings with titanium dioxide have proven to be a challenge. These methods have several disadvantages. The most notable is the preparation of these solutions requires expensive chemicals and the anatase can be unstable. To improve the ability of the anatase to remain stable, coating manufacturers introduce acids. When these coatings are attached to metal surfaces, either they cannot bind or they can damage the metals or substrates due to their low pH values in the finished product. Inorganic sol-gel solutions offer the ability to stabilize the anatase and allow the coating to bind to surfaces after heating at high temperatures. This method of coating a surface is not practical in the real world on existing substrates.

Titanium dioxide has long been known to have decomposition effectiveness when exposed to light, oxygen, and water. Typically, the coatings require under-388 nm UV light to become active. Additives were developed to support the titanium dioxide with iron oxide to add activation in the visible light spectrum. This is valuable for light sources like LED lights that generate white light (with a large blue component) and do not produce UV light. The additive (like iron-oxide) functions as an auxiliary photocatalyst, fed by the photons that are absorbed by the $TiO_2$ crystals. The visible light photons are less energetic, thus resulting in weaker surface activity.

Current methods of manufacturing titanium dioxide typically produce cubic- or rod-shaped crystals with sizes in the 20-100 nm length range. The efficiency of the surface coatings is related to the total effective crystal surface area created by the finished coating. The larger the crystal size, the less the effective surface area, and thus the less the available potential decomposing power that the coating can generate by photocatalytic reactions. Lab experiments have shown that smaller crystals show stronger photocatalytic reactions. Crystals smaller than 20 nm have not been successfully created in an industrial production environment because of the associated complexity of the process.

A limitation of the currently available $TiO_2$ products in the market is that they are difficult to apply to surfaces durably and require constant maintenance and re-application because they demonstrate a relatively limited functional lifetime. One reason is because many such coatings use organic binders that are continuously broken down by the photocatalytic reaction created by the titanium dioxide when exposed to light, oxygen, and water. Another reason is the top surface of the substrate may also be affected by the photocatalytic reaction. This reaction causes the $TiO_2$ surface coating to peel or flake off the substrates to which they are attached.

Another limitation to most existing titanium dioxide coatings is that they only work in areas where light is available. Some antimicrobial coatings use only copper or silver nanoparticles to kill or deactivate bacteria and viruses. Given the way these are designed, the copper is susceptible to being covered by dirt particles or wear off as they react with bacteria and microorganisms. When they get dirty, they stop working relatively quickly because their functional components are blocked by the dirt barrier which prevents the microorganisms from getting in contact with the functional copper or silver particles. These coatings require continuous manual cleaning or reapplication to continue to be effective.

Current methods of applying titanium dioxide coatings including electrostatic spraying, baking, dipping, rolling and brushing. These methods result in uneven surface finishes or are complex and/or expensive. They often require controlled environments like in continuous manufacturing to be applied correctly. Standard combining/mixing with binders results in limited concentrations of functional titanium dioxide particles at the outer surface, which results in less-than-optimal photocatalytic decomposition power. Due to poor adhesion, weaker surface hardness, larger particle sizes or unfavorable mixture ratios of $TiO_2$ particles with binder material, a less than optimal surface coating is created. The $TiO_2$ particles are typically white and leave a haze on smooth dark or transparent surfaces like glass.

Titanium dioxide surface coatings are generally only active in the presence of a UV light source having wavelengths below 388 nm for anatase and below 400 nm for rutile. This is a significant problem in indoor spaces where UV light typically is not present. The rapid adoption of LED light sources further limits the ability of these coatings to function as desired. LED chips emit light between 400-750 nm and contain no UV component in them.

However, these undercoating materials and processes utilizing titanium compounds have problems such as insufficient resistance against the decomposing power of the $TiO_2$ particles that are close to the undercoating materials, lower hydrophilicity, and lower durability of the finished coating.

There is a need in the market for a coating the works in the dark and which can self-clean itself. Copper oxide supported by titanium dioxide, exposed to light, oxygen and water, prevents the copper particles from wearing off the surface and adds the property of self-cleaning the surface—allowing the copper particles to continuously be active over a long period of time.

Also, there are demands for an inorganic film-forming material which is useful as an undercoating material for metal substrates such as steel sheets, aluminum, aluminum alloys or the like, and which can form a film excellent in corrosion resistance and other properties without causing toxicity problems.

However, the ideal surface coating would have either titanium dioxide particles or copper particles supported by titanium dioxide, activated by UV and/or visible light. This coating would have the characteristics of being extremely durable and long lasting—permanent in application. The method of manufacturing and application of a self-cleaning copper oxide-supported titanium dioxide containing peroxo titanium complex is disclosed in the present application.

SUMMARY

A self-cleaning copper oxide, supported by titanium dioxide particles containing peroxo titanium, complex may provide a highly efficient self-cleaning, anti-microbial, antibacterial, anti-viral, anti-fungal, and anti-VOC (Volatile organic compound) permanent surface coating that combines the benefit of a broad-spectrum light-activated photocatalyst and copper oxide.

A self-cleaning composition of titanium dioxide particles containing peroxo titanium complex which may provide a highly efficient self-cleaning, anti-microbial, antibacterial, anti-viral, anti-fungal, and anti-VOC (Volatile organic compound) permanent surface coating that provides the benefit of a broad-spectrum light-activated photocatalyst.

Titanium dioxide offers the ability to self-clean a surface by breaking down organics into harmless gases (such as $H_2O$, $CO_2$, $NO_3$) and allows the added copper oxide particles to remain exposed and continuously provide antimicrobial activity more efficiently by keeping them clean. When copper oxide is attached to the $TiO_2$ crystals properly, and the mix ratio is 0.01-5.0 mass % of the total $TiO_2/Cu_xO$ mass, it adds the benefit of extending the decomposing effect to the coating by visible light or adding antimicrobial properties in complete darkness. In addition, when peroxo titanium complex is included, visible light, UV light, and heating will cause the oxidative decomposition function to be increased, enhancing the function that it can decompose and kill microorganisms such as surrounding organic matter and viruses.

According to one variation, the disclosed self-cleaning—titanium dioxide-supported copper oxide containing peroxo titanium complex addresses all the issues related to previous coatings. The applied coating contains a peroxo titanium complex and copper oxide particles, which allow the coating to function in UV light, visible light, or in the dark. Titanium dioxide constantly cleans the surface when UV light is present, and the combination of the peroxo titanium complex and copper allows the coating to have antiviral and antimicrobial properties in visible light and in the dark areas. The coating has a surface hardness greater than 2H and typically lasts for as long as the substrate exists unless mechanically removed. The surface coating is applied using a spray gun and air compressor or airless sprayer and can be applied to any solid substrate. It is durable, yet flexible so it can adhere to fabrics, flexible surfaces, or hard surfaces equally well.

The surface coating is best applied on an inorganic binder that has an extremely strong bonding strength composed of PTA (Peroxo Titanic Acid). This inorganic binder protects the surface from the decomposing power of the topcoat. The inorganic binder itself is also not sensitive to the decomposing power of the topcoat and therefore prevents the $TiO_2$—$Cu_xO$ topcoat from flaking off the surface. The topcoat contains a higher density of $TiO_2$ particles with a larger functional surface area.

$Cu_2O$ is known as cuprous oxide or Cu(I). CuO is known as cupric oxide or Cu(II). $Cu_xO$ defines a combination of CuO and $Cu_2O$ and has antimicrobial properties with or without light. Cu is not eluted, but a protein-based outer shell of a virus is efficiently adsorbed on the surface of $Cu_2O$ which reduces the microbial titer. $Cu_2O$ has a high ability to denature the protein-based outer shell of a virus. This does not happen with CuO or Ag (silver). Since $Cu_2O$ is an oxide, it will hardly leach out. Over time, $Cu_2O$ decreases in effectiveness as it self-oxidizes into CuO. But when $TiO_2$ and $Cu_xO$ are combined, the anti-microbial effect is restored and sustained because Cu(II) [CuO] gets reduced back to Cu(I) [$Cu_2O$] when visible or UV light is irradiated on the $TiO_2$ particles.

The particles of Titanic Acid (TA) made by the usual method of manufacturing are crystalline and appear to be spindle-shaped and flat. They are typically 20-100 nm in length. This varies widely depending on the production process. Peroxo Titanic Acid is amorphous with no crystallization. It is composed of ions of the general formula $Ti_2(OH)_{x \wedge (x-2)}$, polymerized ions, polymerized clusters of $Ti_2(OH)_2$, etc. The primary particles (if they can be called particles as their size cannot be determined) are thought to be 1 nm or less and their size also varies depending on how they are made. TA is an anisotropic ultra-fine particle that is easy to adhere to, while PTA is close to a liquid. Therefore, a PTA/TA film would have a structure where the TA is surrounded by PTA. When the coating liquid is applied and the film is formed by drying alone, it is physically attached by an anchoring effect. Adhesion develops as it gets caught in the microscopic irregularities of the surface. Since PTA is a liquid-like substance, it can easily penetrate fine, uneven surfaces and solidify as it is, making it easier for adhesion to occur by subsequent layers. The density of the dried film is about 60% of the theoretical density of $TiO_2$, and it changes to a 100% crystalline and dense $TiO_2$ film at 200-250° C.

A semiconductor such as $TiO_2$ absorbs various types of light, causing charge separation and hopping of electrons to a level corresponding to their energy. When light with energy above the band gap is absorbed, it reaches the conductor, and the probability of recombination of electrons and holes decreases. If the $TiO_2$ particles are very small, the electrons have a higher probability of moving to the surface of the particles, resulting in a strong photocatalytic reaction. When CuO clusters are supported, $Cu_xO$ is formed by the reduction of electrons, and exhibits antiviral properties, while on the other hand, electrons are injected into the $TiO_2$ conductors, and photocatalytic activity is exhibited even at visible light energy.

Whether it is $TiO_2$—$Cu_xO$ or $TiO_2$, the photocatalytic activity does not change in principle, because electrons are hopped from the valence band to the conductor if light with a wavelength below 388 nm is irradiated. However, it can be theoretically said that when irradiated by sunlight (which includes ultraviolet and visible light), the recombination probability of electrons and holes is slightly higher, and the activity is slightly improved because the available wavelength range is expanded.

The antimicrobial properties are determined by the components of the coating including $TiO_2$ which may provide organic decomposition by UV light with antimicrobial properties. Combining $TiO_2$ and $Cu_xO$ which may provide organic decomposition in the presence of UV as well as visible light which activates its antimicrobial properties.

This process continues to be antimicrobial due to the action of $Cu_2O$ in the absence of light. $TiO_2$—$Cu_xO$+PTA which may provide organic decomposition by UV or visible light or in the absence of light with antimicrobial properties and the added oxidative action of PTA. PTA has the added benefit of protecting organic substrates from decomposition by the photocatalytic properties of the coating because it is an inorganic in nature.

Visible light can be utilized to cure $TiO_2$ with $Cu_xO$. UV light will cure the coating faster and it will cure more if PTA is present. Drying is sufficient for general exterior and interior walls, as they are not subject to much human physical wear. However, coatings on substrates with a high probability of human contact and where design is important may need to be heated to obtain a strong coating film. Heating is optional to further harden and improve adhesion. Surface hardness and adhesion power are considerably improved between 100-200° C. Furthermore, when PTA is heated to 200-250° C., it changes to $TiO_2$ crystals with photocatalytic activity, resulting in a 100% dense crystalline $TiO_2$ coating film.

The disclosed manufacturing process enables production of titanium dioxide particle sizes between 0.1-20 nm. This smaller particle size increases the coating's decomposing power and durability by more than double of the currently produced $TiO_2$ coatings on the market.

The coating described herein is created by first applying a layer of a PTA-based solvent using a spraying device that can produce a fine mist to wet the surface. The binder is applied in thin coats to produce a homogenous pure PTA inorganic surface followed by several thin coats of $TiO_2$—$Cu_xO$ or applied as a mixed product to form a single fluid surface coating.

Each coat is allowed to dry by air before any next coat is applied. The finalized coating can optionally be heated between 100-250° C. to create a stronger and denser surface structure. Natural curing happens with the use of light to create the final hardness of the coating. The thickness of the final coating may range from 80-1500 nanometers depending on the application and desired decomposing power. The coating can be applied to virtually every permanently solid material, including flexible materials.

Other aspects, embodiments and features of the methods disclosed herein will become apparent from the following detailed description when considered in conjunction with the accompanying figures. The accompanying figures are for schematic purposes and are not intended to be drawn to scale. In the figures, each identical or substantially similar component that is illustrated in various figures is represented by a single numeral or notation. For purposes of clarity, not every component is labeled in every figure. Nor is every component of each embodiment of the device and method shown where illustration is not necessary to allow those of ordinary skill in the art to understand the device and method.

BRIEF DESCRIPTION OF THE DRAWINGS

The preceding summary, as well as the following detailed description of the disclosed methods, will be better understood when read in conjunction with the attached drawings. It should be understood, however, that the disclosed methods are not limited to the precise arrangements and instrumentalities shown.

DETAILED DESCRIPTION

The following detailed description is made with reference to the technology disclosed. Preferred implementations are described to illustrate the technology disclosed, not to limit its scope, which is defined by the claims. Those of ordinary skill in the art will recognize a variety of equivalent variations on the description.

The stable production process described herein allows one to rapidly raise the temperature of the product while preventing the crystals from sticking to internal components. The result is a permanent surface coating that is applied in one or two steps to produce a fully optically transparent surface finish on any substrate, including transparent surfaces like glass, metal, plastic or wood. During the production process, a copper solution is added to allow the coating to function within the visible light spectrum and to add the benefit of antimicrobial activity in the dark. The final mixture contains (to the $TiO_2$ content) copper oxide which bonds onto the anatase $TiO_2$ crystals ranging from about 0.1 nm to about 200 nm in length, and further from about 1 nm to about 20 nm in length.

A surface coating technician or person can use simple tools like a compressed air gun to spray the coating. The result is a uniform surface finish that remains highly photocatalytic for as long as it is attached to the surface and remains on the surface for a very long time (will not flake or peel off a surface easily). The coating creates a self-cleaning antimicrobial surface when illuminated as well as an antimicrobial surface in dark areas.

Definitions

The term "peroxo titanic acid", alternately abbreviated "PTA", as used herein may refer to any titanium complex, polymerized titanium ions, polymerized clusters, or other titanium-containing species that contain one or more peroxo groups. In some embodiments, the PTA may be in a liquid or suspension form, such as in an aqueous suspension. In some embodiments, PTA may be prepared in a step involving mixing hydrogen peroxide with a titanium-containing material, a non-limiting example of which is titanium hydrate or titanium hydroxide. In some embodiments, liquid PTA may be applied to a surface or object and is cured by any appropriate means. In some embodiments, the cured PTA remaining on a surface or object after curing may still be referred to as PTA.

In some embodiments, PTA may be referred to as a binder and may bind to, support, or be otherwise associated with other domains such as nanoparticles. In some embodiments, a cured PTA layer may be said to contain one or more domains and may have one or more of another domain interspersed within its one or more domains. In some embodiments, PTA may comprise one or more additional solvents, components, or additives. In some embodiments, non-limiting exemplary chemical formulas of PTA may be $Ti_2(OH)x^{(x-2)}$, $Ti(OH)3O2H$, $H4TiO5$, polymerized clusters of $Ti2(OH)2$, $RxTi$—$O$—$O$—$TiRx$ (where Rx refers to any number and/or type of ligand on Ti, where R can be independently selected for each occurrence, including polymeric connections to additional Ti atoms through O, peroxo, or other groups), and any structure or formula containing Ti—O—O—Ti moieties. In some embodiments, PTA may not be adequately described by a standard chemical formula and/or may have a non-integer chemical formula if an elemental analysis is performed. It can be understood that any peroxo titanic acid species is considered to be within the scope of the disclosure, and any appropriate reagents to produce peroxo titanic acid are contemplated.

The term "peroxo-modified" as used herein may refer to one or more species modified by one or more peroxo groups. The peroxo groups could be a free peroxo group or could be a peroxo group associated with another species. In some embodiments, titanium dioxide nanoparticles may be peroxo-modified and referred to as "peroxo-modified titanium dioxide nanoparticles". In some embodiments, "peroxo-modified titanium dioxide nanoparticles" may be peroxo-modified by one or more peroxo groups. In some embodiments, the one or more peroxo groups are free peroxo groups or surface-capping peroxo groups. In some embodiments, the one or more peroxo groups may be associated with PTA or another species such as a surface peroxo group on another nanoparticle. It can be appreciated that any nanoparticle modified with one or more peroxo groups may be referred to as "peroxo-modified". A non-limiting example would be peroxo-modified copper oxide nanoparticles. Peroxo-modified nanoparticles may be present in a colloidal solution, or suspension, such as a sol.

The term "titanium dioxide" as used herein may generally refer to a titanium-oxide or titanium dioxide-based material without strictly defining the chemical composition of the material. It can be appreciated that titanium dioxide nanoparticles may have a number of surface and other defects resulting in a compositional deficiency of either Ti or O. A person of skill in the art would immediately appreciate this and understand that the term "titanium dioxide nanoparticle" or even the commonly-used structural formula "TiO2" does not strictly define the atomic composition and rather generally relates to titanium dioxide or compositional variants thereof having varying Ti:O ratios. In some embodiments, titanium dioxide may be best described by an anatase structure, or by a rutile structure. In some embodiments, titanium dioxide nanoparticles may be weakly crystalline. In some embodiments, titanium dioxide nanoparticles may be highly crystalline. In some embodiments, the crystallinity depends upon heating and/or curing steps. In some embodiments, the degree of crystallinity or crystalline structure may change due to exposure to light or other environmental conditions. In some embodiments, the term "titanium dioxide nanoparticle" may describe a titanium dioxide nanoparticle in the particle size range from about 0.1 to about 200 nm, or from about 0.1 to about 100 nm, or from about 0.1 to 50 nm, or from about 0.1 to about 20 nm, or from about 0.1 to about 10 nm, or from about 0.1 to about 5 nm, or from about 0.1 to about 1 nm.

The term "particle size" as used herein may refer to the size or sizes of a plurality of nanoparticles. It can be appreciated that each of the nanoparticles in such a plurality may not have equivalent particle sizes and may be represented by a range of particle sizes. In general, when a particle size range is given, it would be expected that at least some nanoparticles in a given plurality would have a size in the given range. In some embodiments, the average particle size in a given plurality of nanoparticles may be expected to fall within a given particle size range. In some embodiments, nanoparticles are largely spherical and the particle size is essentially a diameter. In some embodiments, nanoparticles are non-spherical or have one or more elongated dimensions and, in such cases, the particle size of a given particle may be the length of the longest dimension.

The term "copper oxide" as used herein may generally refer to a copper oxide material without strictly defining the chemical composition of the material. It can be appreciated that copper oxide nanoparticles may have a number of surface and other defects resulting in a compositional deficiency of either Cu or O. A person of skill in the art would immediately appreciate this and understand that the term "copper oxide nanoparticle" or even the commonly-used structural formulas do not strictly define the atomic composition and rather generally relate to titanium dioxide or compositional variants thereof having varying Cu:O ratios. In some embodiments, the copper in copper oxide has a 1+ oxidation state (i.e., Cu(I)) and may be described by the formula Cu2O. In some embodiments, the copper in copper oxide has a 2+ oxidation state (i.e., Cu(II)) and may be described by the formula CuO. In some embodiments, a mixed-valence copper oxide may be present wherein some Cu atoms have a 1+ oxidation state while others have a 2+ oxidation state. Such a mixed-valence copper oxide may be described by the formula $Cu_xO$. In some embodiments, one or more copper oxide nanoparticles may be supported by one or more titanium dioxide nanoparticles. In some embodiments, copper oxide nanoparticles may be produced from any Cu precursor or species, which together with a solvent may be referred to as a copper-based liquid. In some embodiments, the term "copper oxide nanoparticle" may describe a cluster of Cu and O atoms with as little as a few Cu atoms. In some embodiments, the term "copper oxide nanoparticle" may describe a copper oxide nanoparticle in the particle size range from about 0.1 to about 200 nm, or from about 0.1 to about 100 nm, or from about 0.1 to 50 nm, or from about 0.1 to about 20 nm, or from about 0.1 to about 10 nm, or from about 0.1 to about 5 nm, or from about 0.1 to about 1 nm.

The term "supported by" as used herein may refer to the state of a cluster of atoms or a nanoparticle being attached to, present on the surface of, or adsorbed on another cluster of atoms or a nanoparticle. One nanoparticle may support a plurality of other nanoparticles. In a non-limiting exemplary embodiment, one or more copper oxide nanoparticles may be supported by a titanium dioxide nanoparticle. When a nanoparticle is supported by another nanoparticle, the support or attachment may provide for electronic communication between the nanoparticles, for instance via electron injection or transfer from the conduction band of one nanoparticle to the other; alternatively or concurrently, a hole may be transferred from the valence band of one nanoparticle to the other. It can be appreciated that ground-state communication may be feasible in some systems, however conduction bands must be populated by an energy input, such as light, in order for such charge transfer to occur. In some embodiments, photoinduced charge transfer, or charge transfer due to the presence of light, may occur between copper oxide and titanium dioxide nanoparticles, or between titanium dioxide and copper oxide nanoparticles, when at least one of the nanoparticles is supported on or by the other.

The term "main aqueous stream" may refer to an aqueous stream in a flow process to which one or more feed streams and/or waste streams may branch to or from at various stages in the flow process. The term "aqueous" may refer to the solvent composition being at least partially aqueous, or water-containing. A main aqueous stream may comprise one or more solvents, reagents, chemicals, products, and/or waste products depending upon the stage in the flow process.

It can be appreciated that the composition of the main aqueous stream changes at different stages in the flow process.

The term "aqueous surface coating suspension" as used herein may refer to any described composition comprising a liquid or solvent and one or more nanoparticles. Alternatively, the term "suspension" may be used interchangeably with the terms "colloidal solution", "colloidal suspension", or "sol". In some embodiments, the aqueous surface coating suspension may comprise titanium dioxide nanoparticles. In some embodiments, the aqueous surface coating suspension may comprise titanium dioxide nanoparticles and peroxo titanic acid (PTA) and optionally copper oxide nanoparticles. In some embodiments, an "aqueous surface coating suspension" may comprise titanium dioxide nanoparticles in the particle size range from about 0.1 to about 200 nm, or from about 0.1 to about 100 nm, or from about 0.1 to 50 nm, or from about 0.1 to about 20 nm, or from about 0.1 to about 10 nm, or from about 0.1 to about 5 nm, or from about 0.1 to about 1 nm. In some embodiments, an "aqueous surface coating suspension" may further comprise copper oxide nanoparticles in the particle size range from about 0.1 to about 200 nm, or from about 0.1 to about 100 nm, or from about 0.1 to 50 nm, or from about 0.1 to about 20 nm, or from about 0.1 to about 10 nm, or from about 0.1 to about 5 nm, or from about 0.1 to about 1 nm. In some embodiments, the nanoparticles may be homogeneously distributed and non-aggregated. In some embodiments, the nanoparticles may be partially aggregated or fully aggregated but may remain suspended.

The term "halide-containing" as used herein may be used in reference to a coordination complex to indicate the presence of one or more halide or halogen ligands. In some embodiments, a halide-containing complex may comprise titanium, Ti, in various oxidation states such as IV, III, or II. In some embodiments, the halide ligand may be selected from one or more of F–, Cl–, Br–, and/or I–. In some embodiments, a halide-containing complex may include one or more halide ligands and one or more non-halide ligands. In some embodiments, the complex may be a precursor to one or more chemical reactions. For example, a titanium complex may be referred to as a titanium precursor. In some embodiments, a halide-containing titanium precursor may refer to a titanium complex having one or more F–, Cl–, Br–, and/or I– ligands. A non-limiting exemplary halide-containing titanium precursor may be $TiCl_4$.

The term "a soluble hydroxide of a cation" as used herein may refer to a water soluble hydroxide. In some embodiments, the cation may be an alkali or alkaline ion, or an ammonium ($NH_4^+$) or substituted ammonium. In some embodiments, the cation may be sodium, potassium, calcium, or barium. In some embodiments, the cation may be ammonium, methyl ammonium, ethyl ammonium, or any other substituted ammonium. In some embodiments, the cation is ammonium. In some embodiments, the "soluble hydroxide of a cation" is ammonium hydroxide. Ammonium hydroxide may be alternatively referred to as ammonia.

The term "titanium hydroxide solids" may be used to refer to titanium hydroxide formed by the reaction between a halide-containing titanium precursor and a soluble hydroxide of a cation. In some embodiments, the solids are a precipitate formed within an aqueous solution. In some embodiments, the chemical formula of titanium hydroxide solids is $Ti(OH)_4$. In some embodiments, the halide-containing titanium precursor may be $TiCl_4$ and the soluble hydroxide of a cation may be ammonium hydroxide. In some embodiments, the term "titanium hydrate" may be used instead of "titanium hydroxide" and the two terms may be taken to have the same meaning.

The term "domain" as used herein may refer to a compositional, structural, morphological, or crystallographic portion of a coating. In some embodiments, a domain comprises one or more titanium dioxide nanoparticles and may be referred to as a titanium dioxide domain. In some embodiments, a domain comprises one or more copper oxide nanoparticles and may be referred to as a copper oxide domain. The coatings may comprise one or more PTA domains with one or more titanium dioxide and copper oxide domains dispersed therein.

The term "copper-based liquid" may refer to any copper-containing aqueous reagent useful for forming copper oxide clusters or copper oxide on titanium dioxide nanoparticles or in a peroxo-modified titanium dioxide sol. In some embodiments, the copper-based liquid may contain one or more copper (II) species such as Copper(II) sulfate, Copper(II) chloride, Copper(II) hydroxide, Copper(II) nitrate, Copper (II) oxide clusters or nanoparticles, Copper(II) acetate, Copper(II) fluoride, Copper(II) bromide, Copper(II) carbonate, Copper(II) carbonate hydroxide, Copper(II) chlorate, Copper(II) arsenate, Copper(II) azide, Copper(II) acetylacetonate, Copper(II) aspirinate, Copper(II) cyanurate, Copper (II) glycinate, Copper(II) phosphate, Copper(II) perchlorate, Copper(II) selenite, Copper(II) sulfide, Copper(II) thiocyanate, Copper(II) triflate, Copper(II) tetrafluoroborate, Copper(II) acetate triarsenite, Copper(II) benzoate, Copper(II) arsenite, Copper(II) chromite, Copper(II) gluconate, Copper (II) peroxide, and/or Copper(II) usnate, including anhydrates and/or hydrates thereof. In some embodiments, the copper-based liquid may contain one or more copper (I) species such as Copper(I) chloride, Copper(I) iodide, Copper(I) cyanide, Copper(I) thiocyanate, Copper(I) sulfate, Copper(I) sulfide, Copper(I) acetylide, Copper(I) bromide, Copper(I) oxide, Copper(I) fluoride, Copper(I), hydroxide, Copper(I) hydride, Copper(I) nitrate, Copper(I) phosphide, Copper(I) thiophene-2-carboxylate, and/or Copper(I) t-butoxide, including anhydrates and/or hydrates thereof. In some embodiments, the copper-based liquid may be copper (II) chloride, or $CuCl_2$, dissolved in water.

It can be appreciated that any copper compound that dissolves in water may be useful in a "copper based liquid" and any specific compounds listed in the disclosure are non-limiting to other salts, coordination complexes, or other compounds. In some embodiments, the "copper based liquid" may include inorganic copper compounds such as copper chloride $CuCl_2$, copper diammonium chloride $Cu(NH_4)_2Cl_4$, copper nitrate $Cu(NO_3)_2$, copper sulfate $CuSO_4$, copper carbonate $CuCO_3$, or organic copper compounds such as copper acetate $Cu(CH_3COO)_2$. These copper compounds can be described as water soluble copper compounds. Generally, these copper compounds may have a solubility of about 0.1 mg/mL or greater. In some embodiments, the solubility of the copper compound in water may be from about 1 mg/mL to about 5 g/mL, or from about 10 mg to about 2 g/mL, or from about 100 mg to about 1.5 g/mL, or from about 500 mg to about 1.5 g/mL, or about 0.7 g/mL. These solubilities are generally determined at room temperature, or at about 25° C.

With respect to a time or temperature given by "up to", such as in "up to 24 hours", it can be appreciated that the term represents a range of values from an implied minimum value to the given upper value. For instance, "up to 24 hours" may imply ranges such as from about 1 minute to about 24 hours, or from about 5 minutes to about 24 hours, or from about 30 minutes to about 24 hours, or from about 1 hour to about 24 hours, or from about 4 hours to about 24 hours, or from about 10 hours to about 24 hours. Likewise, the range may be shorter than the given upper limit. For instance, "up to 24 hours" may imply a range from about 1 minute to about 24 hours, or from about 1 minute to about 10 hours, or from about 1 minute to about 5 hours, or from about 1 minute to about 1 hour.

Surface Coatings

A transparent surface coating is disclosed having a composition comprising titanium dioxide particle sizes ranging from about 0.1 nm to about 200 nm in length, and further from about 0.1 nm to about 20 nm in length; a peroxo titanic acid as a binder, and a $TiO_2$ or $TiO_2$—$Cu_xO$ solution. The $TiO_2$ or $TiO_2$—$Cu_xO$ solution may be applied by spraying or any other means and $TiO_2$ or $TiO_2$—$Cu_xO$ and peroxo titanic acid solution may be mixed together or applied separately to create a final surface coating on any substrate material.

Figure 1:
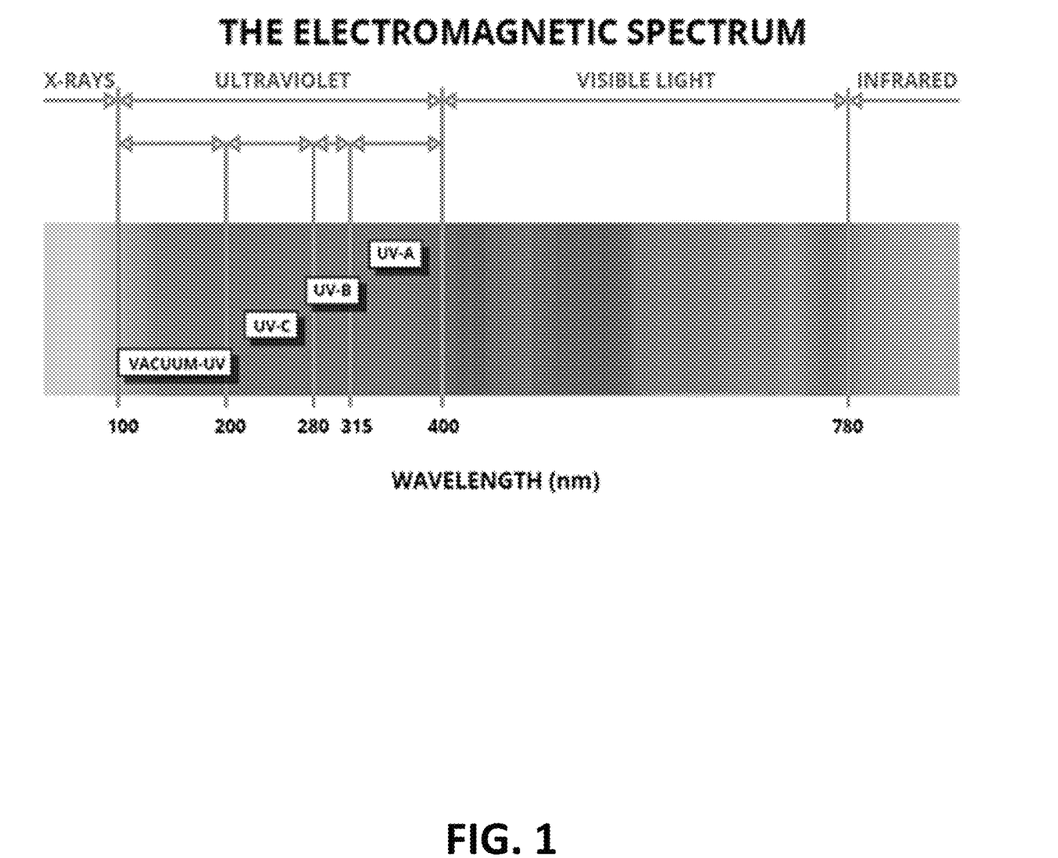
FIG. 1 depicts the electromagnetic spectrum.
Figure 2:
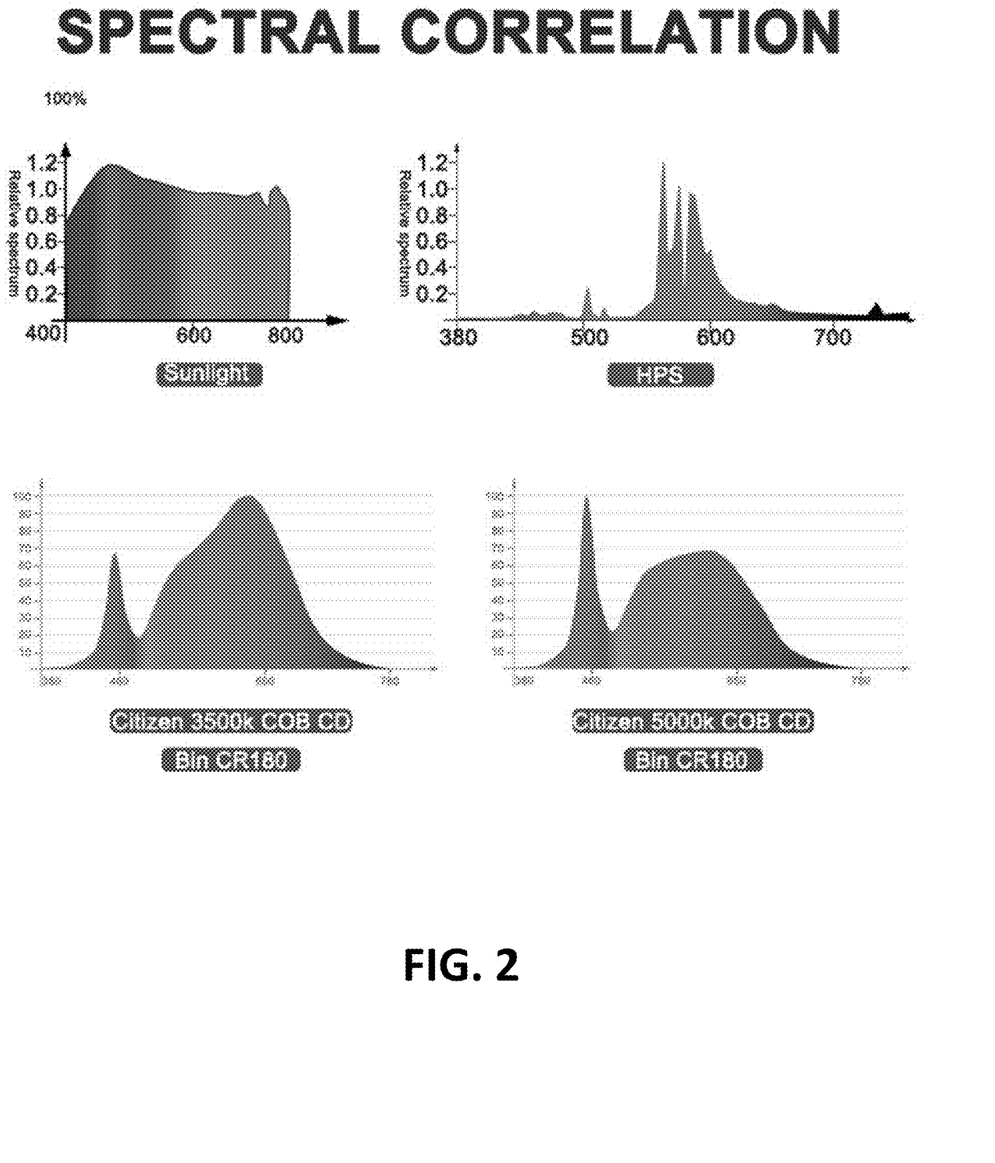
FIG. 2 depicts a spectral correlation of the solar spectrum to various light sources including a high pressure sodium bulb (HPS), a 3500 k LED, and a 5000 k LED.
Figure 3:
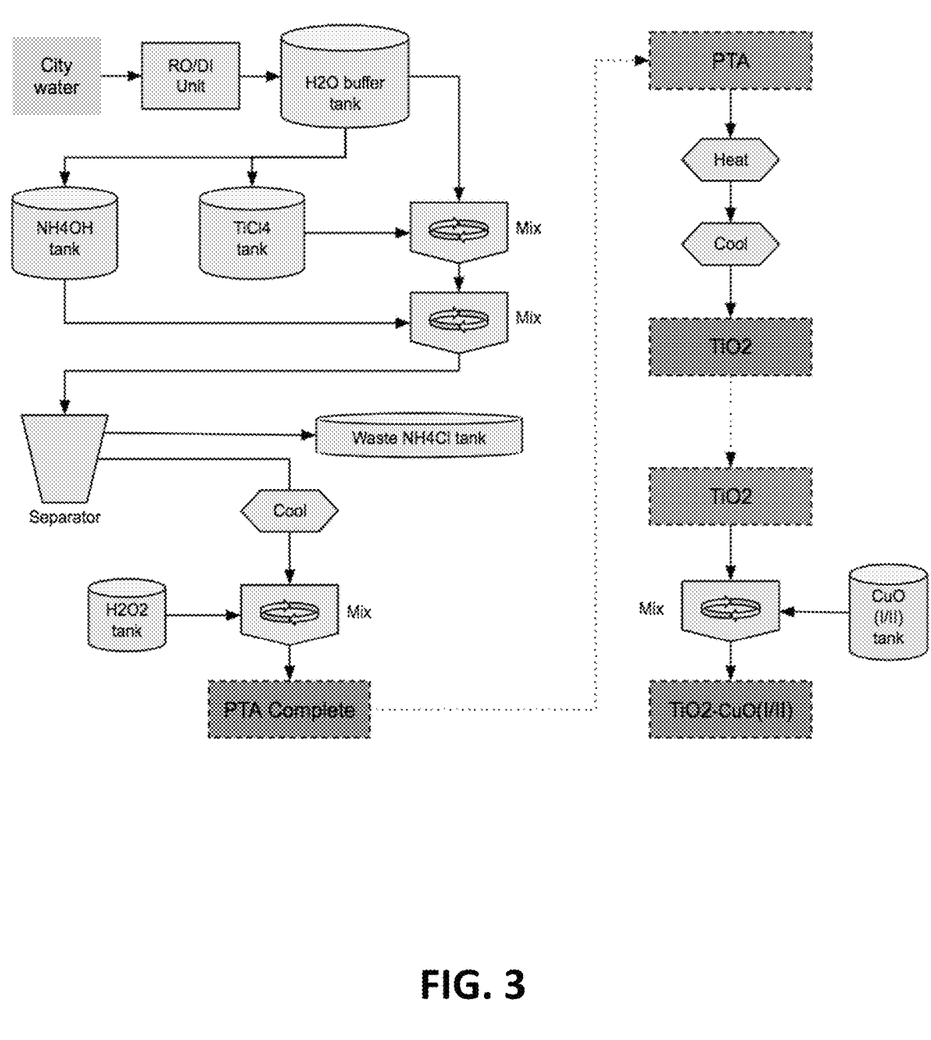
FIG. 3 depicts an illustrative variation of preparing a $TiO_2$—$Cu_xO$ solution.

The process of manufacturing an inorganic titanium dioxide coating which includes various sub-processes described in FIG. 3. These sub-processes are described in the following paragraphs.

A method for preparation of the surface coating composition may include the steps of:

adding Titanium tetrachloride to a main $H_2O$ stream in an actively cooled mixing chamber to create a dilution of 1-17%; diluting a parallel stream of ammonia solution with deionized ultrapure water ($H_2O$) and then adding this to the main fluid stream in the actively cooled mixing chamber so that the mixture has a pH value between 5.5 and 9.0; separating $NH_4^+$ and $Cl^-$ ions from the main fluid using either a cooled modified 3-phase centrifugal separator with added counterflow or an electrolysis separation system and/or a filter membrane type separator with cross-flow $H_2O$ rinsing separation unit; creating a second main fluid stream of deionized ultrapure water ($H_2O$)+titanium hydrate $Ti(OH)_4$ solids and a waste stream of water+$NH_4^+$/$Cl^-$ ions (ammonium chloride solution); obtaining the main fluid stream containing deionized ultrapure water ($H_2O$)+titanium hydrate $Ti(OH)_4$ solids actively cooled between 1-20° C.;

feeding cooled hydrogen peroxide $H_2O_2$ and the main fluid stream of step (a) into the actively cooled mixing chamber to dissolve the $Ti(OH)_4$ solids to form peroxo titanic acid (PTA);

feeding the stream of PTA of step (b) into a positive displacement compressor that will increase the pressure in the main fluid stream to between 2-12 bars; passing the PTA through a heating unit that will increase the temperature of the PTA between 105-300° C. within 120 seconds for a maximum duration of 60 minutes and converting the PTA to peroxo-modified anatase sol (PA);

cooling the PA below 70° C. within 120 seconds to obtain a titanium dioxide coating; and optionally, mixing a copper-based liquid to $TiO_2$ of step (d) in the range of 0.01-5.0 mass % to $TiO_2$ to obtain $TiO_2$—$Cu_xO$ coating composition.

Sub-Process Part 1—Creating Titanium Hydrate:

$$TiCl_4+4NH_4OH \rightarrow H4TiO_4+4NH_4Cl$$

or $$TiCl_4+4NH_4OH \rightarrow Ti(OH)_4+4NH_4Cl$$

The process begins with a cooled main deionized ultrapure water ($H_2O$) fluid stream. Titanium tetrachloride $TiCl_4$ is added to the main $H_2O$ stream in a cooled mixing chamber to create a dilution of 1-17%. A parallel stream of ammonia solution is diluted with deionized ultrapure water ($H_2O$) and then added to the main fluid stream in a cooled mixing chamber so that the mixture ends up with a pH value between 5.5 and 9.0. The concentration and pH levels are constantly monitored throughout the process to control the chemistry.

The main fluid stream now contains $NH_4^+$ and $Cl^-$ ions which will be separated from the main fluid stream using either a cooled modified 3-phase centrifugal separator with added counterflow or an electrolysis separation system and/or a filter membrane type separator with cross-flow $H_2O$ rinsing separation unit. This will create a new main fluid stream of deionized ultrapure water ($H_2O$)+titanium hydrate $Ti(OH)_4$ solids and a waste stream of water+$NH_4^+$/$Cl^-$ ions (ammonium chloride solution). The main fluid stream containing deionized ultrapure water ($H_2O$)+titanium hydrate $Ti(OH)_4$ solids is now actively cooled between 1-20° C.

Sub-Process Part 2—Creating Peroxo Titanic Acid (PTA):

$$H_4TiO_4+H_2O_2 \rightarrow Ti_2O_5(OH)_2$$

Cooled hydrogen peroxide $H_2O_2$ and the main fluid stream are fed into an actively cooled mixing chamber to dissolve the $Ti(OH)_4$ solids to form peroxo titanic acid (PTA). This concludes the PTA production. The PTA may now be stored below 20° C. to be used and mixed as a main component in the binder solution or it may be the feed for the production process of the photocatalytic anatase $TiO_2$ solution.

Process Part 3—Converting PTA to TA:

$$Ti_2O_5(OH)_{x(x-2)}^- \rightarrow 2TiO_2+(x-2)OH^-+H_2O+O_2$$

A stream of PTA is fed into a positive displacement compressor that will increase the pressure in the main fluid stream to between 2-12 bars. The PTA will then pass through a heating unit that will increase the temperature of the PTA between 105-300° C. within 120 seconds for a maximum duration of 60 minutes. This converts the PTA to peroxo-modified anatase sol (PA).

After passing through the heating unit, the fluid stream passes through a cooling unit, which cools the PA below 70° C. within 120 seconds. After cooling the fluid, the pressure is reduced to atmospheric. Optionally, at this point, a copper-based liquid in the range of 0.01-5.0 mass % to $TiO_2$ may be mixed with the PA to add visible light photocatalytic properties+antimicrobial properties in the dark.

The following process describes the production of PTA (peroxo titanic acid) in steps.

Cooled aqueous titanium tetrachloride $TiCl_4$ and ammonium water $NH_4OH$ solutions are combined to form titanium hydrate $H_4TiO_4$ solids according to the formula:

$$TiCl_4+4NH_4OH \rightarrow H_4TiO_4+4NH_4Cl.$$

The solids are separated by either a modified 3-phase centrifugal separator with added counterflow rinsing or a membrane type separator with crossflow rinsing of the solids to remove the $NH_4^+$ and Cl- ions.

It will be understood by a person skilled in the art that forming titanium hydrate can be conducted using various reactions with any 'titanium chloride' base solution. For example, it can be formed according to the following formula:

$$2TiCl_3+2HCl+8NH_4OH \rightarrow 2Ti(OH)_4+8NH_4Cl+H_2; \text{ or}$$

according to a formula:

$$TiOCl_2+2NH_4OH+3H_2O \rightarrow Ti(OH)_4+2NH_4Cl+2H_2O;$$ or any other suitable reaction containing any 'titanium chloride' base solution.

To finalize this PTA process, the rinsed titanium hydrate $H_4TiO_4$ solids are mixed with hydrogen peroxide $H_2O_2$ in an actively cooled mixing unit which creates the primary product peroxo titanic acid Ti2O5(OH)$_2$ according to the formula:

$$H_4TiO_4 + H_2O_2 \rightarrow Ti_2O_5(OH)_2$$

The following process describes the production of TiO$_2$ (anatase) in steps:

The PTA is pressurized between 2 to 12 bars, then rapidly heated within 120 seconds between 105-300° C. for a maximum of 60 minutes which creates peroxo-modified anatase sol (PA) according to the formula:

$$Ti_2O_5(OH)_{x(x-2)}^- \rightarrow 2TiO_2 + (x-2)OH + H_2O + O_2$$

The PA is then rapidly cooled within 120 seconds below 70° C. to the final product TiO2 (anatase), which completes the <20 nm crystal size TiO$_2$ production process.

The following process describes the production of TiO2-Cu$_x$O in steps:

A copper-based liquid is mixed with the TiO$_2$ (anatase) solvent in the range of 0.01-5.0 mass % to TiO$_2$ to bind Cu$_x$O onto the TiO$_2$ crystals.

Figure 4:
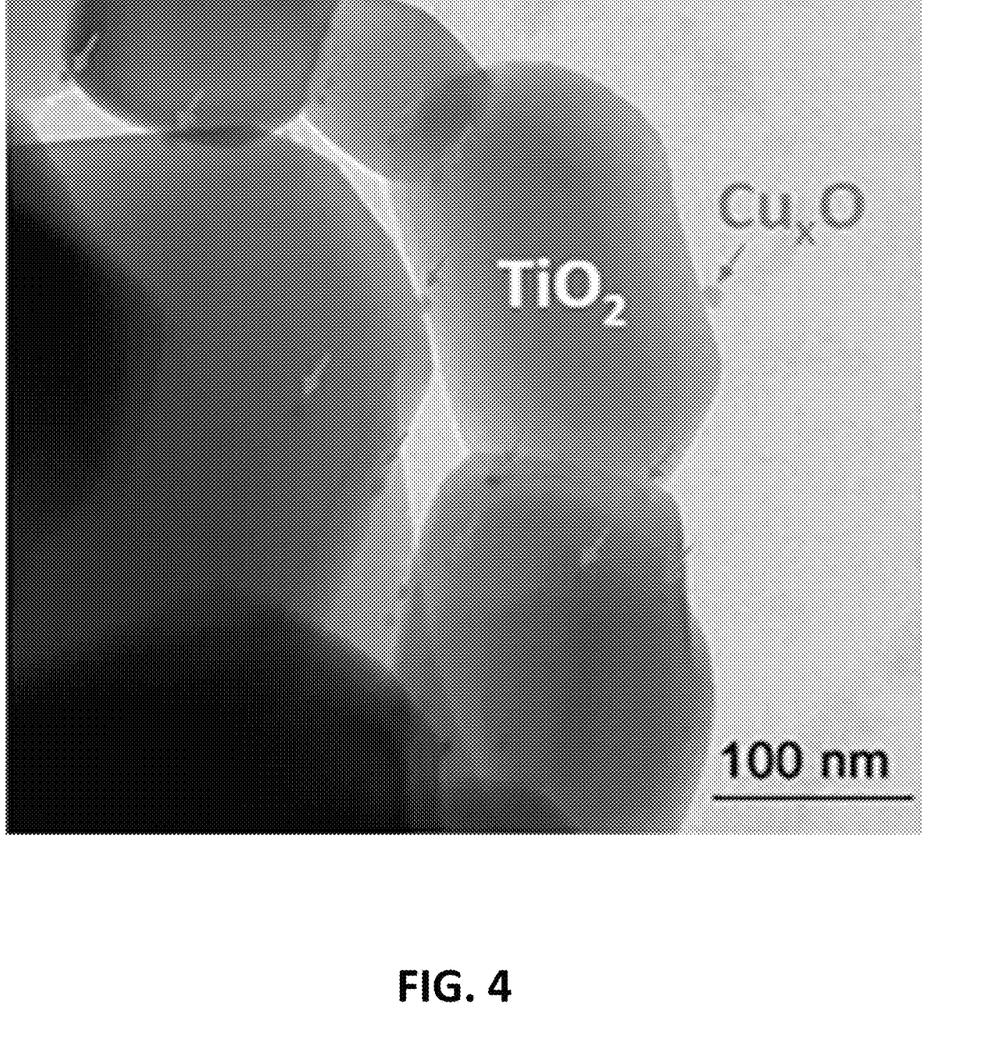
FIG. 4 depicts an illustrative variation of anatase titanium dioxide crystals with $Cu_xO$ particles attached.

FIG. 4 illustrates the microstructure for the surface coating composition.

The various sub-processes in combination complete the production of a novel coating solution that is composed of TiO$_2$ particles optionally loaded with Copper. The desired coating material so produced is bonded to surfaces in combination with Peroxo Titanic acid, to create a uniform surface coating that functions in UV and/or visible light, as well as in darkness.

This unique manufacturing process enables production of titanium dioxide particle sizes between 0.1-20 nm. This smaller particle size increases the coating's decomposing power and durability by more than double of the currently produced TiO$_2$ coatings on the market.

Titanium dioxide offers the ability to self-clean the surface by breaking down organics into harmless gases (such as H$_2$O, CO$_2$, NO$_3$) and allows the added copper oxide particles to remain exposed and continuously do their antimicrobial job more efficiently by keeping them clean. When copper oxide is attached to the TiO$_2$ crystals properly, it adds the benefit of extending the decomposing effect to the coating by visible light or adding antimicrobial properties in complete darkness. In addition, when the peroxo titanium complex is included, visible light, UV light, and heating will cause the oxidative decomposition function to be increased, enhancing the function that it can decompose and kill microorganisms such as surrounding organic matter and viruses.

The surface coating is applied using a spray gun and air compressor or airless sprayer and can be applied to any solid substrate. The dried surface coating is durable, yet flexible so it can adhere to fabrics, flexible surfaces, or hard surfaces equally well.

Several non-limiting exemplary variations are listed below.

According to variation 1, a surface coating may include a peroxo titanic acid as a binder and at least one of a TiO$_2$ or TiO$_2$—Cu$_x$O solution comprising titanium dioxide particle sizes ranging from about 0.1-200 nm.

Variation 2 may include a surface coating as set forth in variation 1, wherein said at least one of TiO$_2$ or TiO$_2$—Cu$_x$O solution and peroxo titanic acid are applied to a surface separately to sanitize the surface.

Variation 3 may include a surface coating as set forth in any of variations 1 through 2, wherein the titanium dioxide particle sizes range from about 0.1-20 nm.

Variation 4 may include a surface coating as set forth in any of variations 1 through 3, wherein said surface coating has self-cleaning, antiviral, anti-bacterial, anti-fungal, and other antimicrobial properties.

Variation 5 may include a surface coating as set forth in any of variations 1 through 4, wherein said surface coating has a pH ranging from about 5.5-9.0.

Variation 6 may include a surface coating as set forth in any of variations 1 through 5, wherein the surface coating is transparent.

According to variation 7, a method for manufacturing of a titanium dioxide coating may include the steps of adding titanium tetrachloride to a main H$_2$O stream in an actively cooled mixing chamber to create a dilution of 1-17%; diluting a parallel stream of ammonia solution with deionized ultrapure water; adding the parallel stream of ammonia solution to the main H$_2$O stream in a cooled mixing chamber to create a main fluid such that the main fluid has a pH value between 5.5 and 9.0; separating NH$_4^+$ and Cl$^-$ ions from the main fluid using at least one of a cooled modified 3-phase centrifugal separator with added counterflow, an electrolysis separation system, or a filter membrane type separator with cross-flow H$_2$O rinsing separation unit; creating a second main fluid stream comprising deionized ultrapure water (H$_2$O) and titanium hydrate Ti(OH)$_4$ solids and a waste stream of water comprising NH$_4^+$/Cl$^-$ ions; obtaining the main fluid stream containing deionized ultrapure water (H$_2$O)+titanium hydrate Ti(OH)$_4$ solids actively cooled between 1-20° C.; feeding cooled hydrogen peroxide H$_2$O$_2$ and the main fluid stream into the actively cooled mixing chamber to dissolve the Ti(OH)$_4$ solids to form peroxo titanic acid (PTA); feeding the stream of PTA into a positive displacement compressor and increasing the pressure of the main fluid stream to about 2 to 12 bars; passing the PTA through a heating unit and increasing the temperature of the PTA to about 105-300° C. converting the PTA to peroxo-modified anatase sol (PA); and cooling the PA below 70° C. within 120 seconds to obtain the titanium dioxide coating.

Variation 8 may include a method for manufacturing of a titanium dioxide coating as set forth in variation 7, further comprising mixing a copper-based liquid to TiO$_2$ in the range of 0.01-5.0 mass % to TiO$_2$.

Variation 9 may include a method for manufacturing of a titanium dioxide coating as set forth in any of variations 7 through 8, wherein the titanium dioxide coating comprises anatase TiO$_2$ crystals ranging from about 0.1 nm to about 20 nm in size.

Variation 10 may include a method for manufacturing of a titanium dioxide coating as set forth in any of variations 7 through 9, wherein the titanium dioxide coating is transparent.

Variation 11 may include a method for manufacturing of a titanium dioxide coating as set forth in any of variations 7 through 10, wherein the peroxo-modified anatase sol is created by applying heat above 110° C. to the PTA solution in a pressurized continuous flow production.

Variation 12 may include a method for manufacturing of a titanium dioxide coating as set forth in any of variations 7 through 11, wherein the titanium dioxide coating comprises 0.01-5.0 mass % copper oxide.

Variation 13 may include a method of providing a self-cleaning, deodorizing, and antimicrobial coating comprising providing a TiO$_2$ or TiO$_2$—Cu$_x$O coating comprising peroxo titanic acid and at least one of spraying, dipping, or pouring TiO$_2$ or TiO$_2$—Cu$_x$O coating comprising peroxo titanic acid on a surface.

Variation 14 may include a method of providing a self-cleaning, deodorizing, and antimicrobial coating as set forth in variation 13, wherein providing a $TiO_2$ or $TiO_2$—$Cu_xO$ coating comprising peroxo titanic acid further comprises mixing the $TiO_2$ or $TiO_2$—$Cu_xO$ coating comprising peroxo titanic acid in solution to provide a single fluid surface coating.

Variation 15 may include a method of providing a self-cleaning, deodorizing, and antimicrobial coating as set forth in any of variations 13 through 14, wherein at least one of spraying, dipping, or pouring $TiO_2$ or $TiO_2$—$Cu_xO$ coating comprising peroxo titanic acid on a surface comprises at least one of spraying, dipping, or pouring a plurality of times.

Variation 16 may include a method of providing a self-cleaning, deodorizing, and antimicrobial coating as set forth in any of variations 13 through 15, wherein the $TiO_2$ or $TiO_2$—$Cu_xO$ coating comprising peroxo titanic acid is heated to a temperature ranging from about 100 to about 250° C. for up to 24 hours.

Variation 17 may include a method of providing a self-cleaning, deodorizing, and antimicrobial coating as set forth in any of variations 13 through 16, wherein the thickness of the $TiO_2$ or $TiO_2$—$Cu_xO$ coating comprising peroxo titanic acid ranges from about 80 nm to about 1500 nm.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements.

The foregoing detailed description is merely exemplary in nature and is not intended to limit the invention or application and uses of the invention. Furthermore, there is no intention to be bound by any expressed or implied theory presented in the preceding technical field, background, brief summary, or the following detailed description.

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and systems of the present invention, where the term comprises is used with respect to the recited steps of the methods or components of the compositions, it is also contemplated that the methods and compositions consist essentially of, or consist of, the recited steps or components. Furthermore, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

Furthermore, it should be recognized that in certain instances a composition can be described as being composed of the components prior to mixing, because upon mixing certain components can further react or be transformed into additional materials.

All percentages and ratios used herein, unless otherwise indicated, are by weight.

What is claimed is:

1. A continuous flow method for producing an aqueous titanium dioxide surface coating suspension, comprising the steps of:
    a. providing a main aqueous stream having a halide-containing titanium precursor and a soluble hydroxide of a cation;
    b. separating the cation of the soluble hydroxide and halide ions from the main aqueous stream using a separator, wherein the main aqueous stream exiting the separator contains titanium hydroxide solids;
    c. cooling the main aqueous stream exiting the separator and containing titanium hydrate solids to between about 1 to about 40° C.;
    d. mixing the cooled main aqueous stream containing titanium hydroxide solids with hydrogen peroxide in an actively cooled mixing chamber to produce peroxo titanic acid (PTA) in the main aqueous stream;
    e. passing the main aqueous stream containing PTA through a heating unit and increasing the temperature to about 105-300° C., wherein the heating converts at least a portion of the PTA to a peroxo-modified anatase sol (PA); and
    f. cooling the main aqueous stream exiting the heating unit to below 70° C. to obtain the aqueous titanium dioxide surface coating suspension.

2. The method of claim 1, wherein step (a.) comprises the sequential steps of:
    i. providing a first aqueous feed stream having a halide-containing titanium precursor, and a parallel second aqueous feed stream having a soluble hydroxide of a cation;

ii. adding the first aqueous feed stream to a main aqueous stream in a first actively cooled mixing chamber to create a dilution of the titanium precursor of about 1 to about 17%;

iii. combining the second aqueous feed stream with the main aqueous stream exiting the first actively cooled mixing chamber in a second actively cooled mixing chamber such that the resulting aqueous stream has a pH value of about 5.5 to about 9.0.

3. The method of claim 1, wherein the soluble hydroxide of a cation is ammonium hydroxide and wherein step (b.) comprises separating $NH_4^+$ and halide ions from the main aqueous stream exiting the second actively cooled mixing chamber using at least one separator selected from the group consisting of a cooled modified 3-phase centrifugal separator with added counterflow, an electrolysis separation system, a filter membrane type separator with cross-flow $H_2O$ rinsing separation unit, and combinations thereof, wherein the separating creates an aqueous waste stream having $NH_4^+$ and halide ions that is disposed of, and wherein the main aqueous stream exiting the separator contains titanium hydroxide solids.

4. The method of claim 1 comprising, the further step of pressurizing the main aqueous stream after step (d) and prior to step (e), wherein the pressurizing is accomplished by a positive displacement compressor to increase the pressure of the main aqueous stream to a pressure of about 2 to about 12 bars.

5. The method of claim 1, wherein the halide-containing titanium precursor is titanium tetrachloride and wherein the halide ions separated in step (b.) are $Cl^-$ ions.

6. The method of claim 1, wherein the peroxo-modified anatase sol comprises peroxo-modified titanium dioxide nanoparticles with a particle size having a range selected from the group consisting of from about 0.1 to about 200 nm, from about 0.1 to about 100 nm, from about 0.1 to about 50 nm, from about 0.1 to about 20 nm, from about 0.1 nm to about 10 nm, from about 0.1 to about 5 nm, or from about 0.1 to about 1 nm.

7. The method of claim 1, wherein the cooling step (f.) is performed within 200 seconds of the heating step (e.).

8. The method of claim 7, wherein the peroxo-modified anatase sol comprises peroxo-modified titanium dioxide nanoparticles with a particle size of about 0.1 to about 20 nm.

9. The method of claim 1, wherein the cooling step (f.) is performed within 120 seconds of the heating step (e.).

10. The method of claim 1, further comprising the step of mixing a copper-based liquid with the obtained aqueous titanium dioxide surface coating suspension to obtain a coating composition having titanium dioxide and copper oxide.

11. The method of claim 10, wherein the copper oxide is present at about 0.01% to about 5% by weight of titanium dioxide.

12. The method of claim 10, wherein the copper-based liquid is an aqueous reagent.

13. The method of claim 12, wherein the copper-based liquid comprises one or more of a copper (II) species selected from the group consisting of Copper(II) sulfate, Copper(II) chloride, Copper(II) hydroxide, Copper(II) nitrate, Copper(II) oxide clusters or nanoparticles, Copper (II) acetate, Copper(II) fluoride, Copper(II) bromide, Copper (II) carbonate, Copper(II) carbonate hydroxide, Copper(II) chlorate, Copper(II) arsenate, Copper(II) azide, Copper(II) acetylacetonate, Copper(II) aspirinate, Copper(II) cyanurate, Copper(II) glycinate, Copper(II) phosphate, Copper(II) perchlorate, Copper(II) selenite, Copper(II) sulfide, Copper (II) thiocyanate, Copper(II) triflate, Copper(II) tetrafluoroborate, Copper(II) acetate triarsenite, Copper(II) benzoate, Copper(II) arsenite, Copper(II) chromite, Copper(II) gluconate, Copper(II) peroxide, and Copper(II) usnate, including anhydrates and hydrates thereof.

14. The method of claim 12, wherein the copper-based liquid comprises one or more of a copper (I) species selected from the group consisting of Copper(I) chloride, Copper(I) iodide, Copper(I) cyanide, Copper(I) thiocyanate, Copper(I) sulfate, Copper(I) sulfide, Copper(I) acetylide, Copper(I) bromide, Copper(I) oxide, Copper(I) fluoride, Copper(I), hydroxide, Copper(I) hydride, Copper(I) nitrate, Copper(I) phosphide, Copper(I) thiophene-2-carboxylate, and Copper (I) t-butoxide, including anhydrates and hydrates thereof.

15. The method of claim 12, wherein the copper-based liquid comprises a copper compound having a solubility in water in a range selected from the group consisting of from about 1 mg/mL to about 5 g/mL, from about 10 mg/mL to about 2 g/mL, from about 100 mg/mL to about 1.5 g/mL, and from about 500 mg/mL to about 1.5 g/m L.

16. The method of claim 10, wherein the resultant surface coating suspension comprises peroxo titanic acid, peroxo-modified titanium dioxide nanoparticles, and copper oxide nanoparticles, wherein the titanium dioxide and copper oxide nanoparticles each independently have a particle size from about 0.1 to about 200 nm.

17. The method of claim 16, wherein the titanium dioxide and copper oxide nanoparticles each independently have a particle size in a range selected from about 0.1 to about 100 nm, from about 0.1 to about 50 nm, from about 0.1 to about 20 nm, from about 0.1 to about 10 nm, from about 0.1 to about 5 nm, and from about 0.1 to about 1 nm.

18. The method of claim 6, wherein the resultant surface coating suspension has a pH from about 5.5 to about 9.0.

19. The method of claim 1, wherein the resultant surface coating suspension comprises copper oxide nanoparticles supported by the titanium dioxide nanoparticles.

20. A continuous flow method for producing a peroxo titanic acid (PTA) binder, comprising the steps of:
a. providing a main aqueous stream having a halide-containing titanium precursor and a soluble hydroxide of a cation;
b. separating the cation of the soluble hydroxide and halide ions from the main aqueous stream using a separator, wherein the main aqueous stream exiting the separator contains titanium hydroxide solids;
c. cooling the main aqueous stream exiting the separator and containing titanium hydrate solids to between about 1 to about 40° C.; and
d. mixing the cooled main aqueous stream containing titanium hydroxide solids with hydrogen peroxide in an actively cooled mixing chamber to produce PTA in the main aqueous stream.

21. The method of claim 20, wherein step (a.) comprises the sequential steps of:
i. providing a first aqueous feed stream having a halide-containing titanium precursor, and a parallel second aqueous feed stream having a soluble hydroxide of a cation;
ii. adding the first aqueous feed stream to a main aqueous stream in a first actively cooled mixing chamber to create a dilution of the titanium precursor of about 1 to about 17%;
iii. combining the second aqueous feed stream with the main aqueous stream exiting the first actively cooled mixing chamber in a second actively cooled mixing chamber such that the resulting aqueous stream has a pH value of about 5.5 to about 9.0.

22. The method of claim 20, wherein the soluble hydroxide of a cation is ammonium hydroxide and wherein step (b.) comprises separating $NH_4^+$ and halide ions from the main aqueous stream exiting the second actively cooled mixing chamber using at least one separator selected from the group consisting of a cooled modified 3-phase centrifugal separator with added counterflow, an electrolysis separation system, a filter membrane type separator with cross-flow $H_2O$ rinsing separation unit, and combinations thereof, wherein the separating creates an aqueous waste stream having $NH_4^+$ and halide ions that is disposed of, and wherein the main aqueous stream exiting the separator contains titanium hydroxide solids.

23. The method of claim 20, wherein the halide-containing titanium precursor is titanium tetrachloride and wherein the halide ions separated in step (b.) are $Cl^-$ ions.

* * * * *